(12) United States Patent
Li et al.

(10) Patent No.: US 8,759,355 B2
(45) Date of Patent: Jun. 24, 2014

(54) ARYL PYRIMIDINE DERIVATIVES, PREPARATION METHODS AND PHARMACEUTICAL USES THEREOF

(75) Inventors: Song Li, Beijing (CN); Yanbo Yang, Beijing (CN); Junhai Xiao, Beijing (CN); Wu Zhong, Beijing (CN); Zhibing Zheng, Beijing (CN); Xingzhou Li, Beijing (CN); Yunde Xie, Beijing (CN); Lili Wang, Beijing (CN); Hongying Liu, Beijing (CN)

(73) Assignee: Institute of Pharmacology and Toxicology Academy of Military Medical Sciences P.L.A., Beijing (CN)

( * ) Notice: Subject to any disclaimer, the term of this patent is extended or adjusted under 35 U.S.C. 154(b) by 1038 days.

(21) Appl. No.: 12/670,464

(22) PCT Filed: Jul. 18, 2008

(86) PCT No.: PCT/CN2008/001339
§ 371 (c)(1),
(2), (4) Date: Sep. 27, 2010

(87) PCT Pub. No.: WO2009/012650
PCT Pub. Date: Jan. 29, 2009

(65) Prior Publication Data
US 2011/0009427 A1    Jan. 13, 2011

(51) Int. Cl.
*A61K 31/505*    (2006.01)
*C07D 239/24*    (2006.01)

(52) U.S. Cl.
USPC .......................................... 514/256; 544/335

(58) Field of Classification Search
USPC .......................................... 514/256; 544/335
See application file for complete search history.

(56) References Cited

U.S. PATENT DOCUMENTS

2005/0096337 A1* 5/2005 Ackermann et al. .......... 514/277

FOREIGN PATENT DOCUMENTS

WO    WO2005/047268 A2    5/2005
WO    WO2005/113506 A1    12/2005

OTHER PUBLICATIONS

J. Auwerx et al., "Transcriptional control of triglyceride metabolism: fibrates and fatty acids change the expression of the LPL and apo C-III genes by activating the nuclear receptor PPAR", *Atherosclerosis* (1996), 124 Suppl., S29-S37.
O. Braissant et al., "Differential Expression of Peroxisome Proliferator-Activated Receptors (PPARs): Tissue Distribution of PPAR-α, -β, and -γ in the Adult Rat", *Endocrinology* (1995), 137, 354-366.
R. Epple et al., "1,3,5-Trisubstituted aryls as highly selective PPARδ agonists", *Bioorganic & Medicinal Chemistry Letters* (2006), 16(11), 2969-2973 (ISSN: 0960-894X).
J.M. Lehmann et al., An Antidiabetic Thiazolidinedione Is a High Affinity Ligand for Peroxisome Proliferator-activated Receptor γ (PPARγ) *J. Biol. Chem.* (1995), 270 12953-12956.
K. Schoonjans et al., "Role of the peroxisome proliferator-activated receptor (PPAR) in mediating the effects of fibrates and fatty acids on gene expression", *J. Lipid., Res.* (1996), 37, 907-925.
S.Y. Solodukhin et al., "Phenoxydifluoromethyl Substituted Nitrogen Heterocycles. Synthesis and Heterocyclization Reactions of Ethyl 4,4-Difluoro-4-phenoxyacetoacetate", *Molecules* (2004), 9(3), 164-169 (ISSN: 1420-3049).
B. Staels et al., "Role of PPAR in the Pharmacologial Regulation of Lipoprotein Metabolism by Fibrates and Thiazolidinediones", *Curr. Pharm. Des.* (1997), 3, 1-14.
A. Vidal-Puig et al., "Regulation of PPAR γ Gene Expression by Nutrition and Obesity in Rodents", *J. Clin. Invest* (1996), 97: 2553-2561.

* cited by examiner

*Primary Examiner* — Kamal Saeed
*Assistant Examiner* — Ebenezer O Sackey
(74) *Attorney, Agent, or Firm* — Brinks Gilson & Lione

(57) ABSTRACT

The present invention relates to a compound of formula (I), or a pharmaceutically acceptable salt or solvate thereof. Various substituents in the formula (I) are as defined in the specification. The present invention also relates to a pharmaceutical composition comprising the compound of formula (I), the preparation method of compound of formula (I), and the use of the compound for the preparation of a medicament for treating and/or preventing human peroxisome proliferators activated receptor δ (hPPARδ)-associated diseases and risk factors.

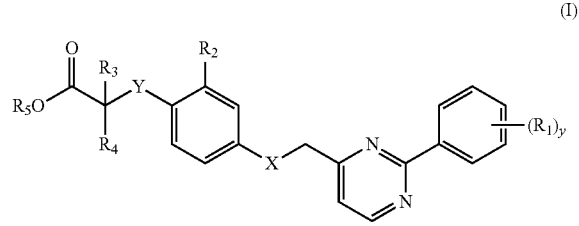

14 Claims, No Drawings

ARYL PYRIMIDINE DERIVATIVES, PREPARATION METHODS AND PHARMACEUTICAL USES THEREOF

TECHNICAL FIELD

The present invention relates to novel compounds, particularly to derivatives of arylpyrimidines that can activate human peroxisome proliferators activated receptor δ (hPPARδ), their preparation methods, a pharmaceutical composition comprising said compounds, and the use of said compounds for the preparation of a medicament for treating and/or preventing hPPARδ-mediated diseases or disorders.

BACKGROUND ART

Peroxisome proliferation factor activated receptor (PPAR) and glucocorticoid receptor, tretinoin receptor and thyroxine receptor belong to ligand dependent transcription factor of nuclear receptor superfamily. Up to now, it has been found that PPARs have three subtypes: α, γ and δ (also called as β), which are encoded by different genes. Moreover, due to the difference of promoter and jointing manner, PPARγ is also divided into two isoforms: $\gamma_1$ and $\gamma_2$, both are different only in the sequence of N end (Visal-Puig, J. Clin. Invest., 97: 2553-2561, 1996). When activated by specific small molecules, PPARs can interact with PPARs reaction elements (PPRE) in promoter region of target gene to modulate the expression of the gene. PPARs is an important transcription modulation factor of metabolism of glucose, lipids and cholesterols in vivo.

PPARα is primarily expressed in the tissue exhibiting rather high decomposition and metabolism activity, such as brown fat tissue and liver, and secondly expressed in kidney, heart and skeletal muscle (Endocrinology, 1995, 137, 354). It can positively or negatively control the expression of genes related to fatty acid metabolism and intra-cellular conveying (e.g. acetyl CoA synthase, fatty acid binding protein and lipoprotein lipase) and apoprotein (AI, AII, CIII) genes related to the metabolism of cholesterol and neutral lipids. PPARγ is mainly present in fat tissue and also present in small quantity in skeletal muscle, liver, colon, retina, immune system. Recently study results show that it is highly expressed in macrophages, including foam cells of atherosclerosis. $PPAR\gamma_2$ is mainly exclusively expressed in fat tissue, while $PPAR\gamma_1$ has been found in various tissues, in which the expression in kidney, intestines and heart is the highest. PPARγ mainly modulates the expression of genes related to fatty cells differentiation and insulin sensitivity (J. Lipid. Res., 1996, 37, 907). PPARδ is distributed widely and expressed in many tissues, wherein the expression in intestines, kidney, heart is the highest. The activation of PPARδ has shown the increase of HDL level and reduction of LDL and VLDL level.

Thiazolinediones drugs, such as, rosiglitazone, show in clinic the enhancement of insulin of diabetes type II patients, reduction of serum glucose. It has been reported thiazolinediones are effective and selective activators of PPARγ and directly bind to PPRRγ (J. M. Lehmann, et al. J. Biol. Chem. 12953-12956, 270 (1995)).

Fibrates drugs have been widely used as therapeutic agents of hyperlipidemia. They can reduce serum triglyceride (20-50%), LDLc (10-15%), and increase HDLc (10-15%). Experiments have shown that the action of fibrates to serum lipids is mediated by activation of PPARα, see, e.g. B. Staels, et al. Curr. Pharm. Des., 1-14, 3(1), (1997). The activation of PPARα leads to the transcription of enzymes that increase the decomposition and metabolism of fatty acids and decrease the resynthesis of fatty acids in liver (causing the reduction of the synthesis of triglyceride and production/secretion of VLDL). Besides, PPARα activation reduces the production of apoC-III. The reduction of the production of apoC-III (an inhibitor of LPL activity) increases the clearance of VLDL (J. Auwerx, et al, Atherosclerosis, J59-S37, 124 (Suppl), (1996)).

PPAR is related to many biological courses and diseases conditions, including hypercholesterolemia, dyslipidemia and diabetes. However, the action of present drugs is not ideal due to toxic and side-effect. Therefore, a safe and effective PPAR agonist drug is needed, which can selectively activate one subtype, or activate multiple subtypes simultaneously.

SUMMARY OF THE INVENTION

The purpose of the present invention is to find and develop small molecular compounds having hPPARδ agonist activity used for treating hPPARδ-mediated diseases, risk factors or conditions, such as lipid abnormality, hyperlipidemia, hypercholesterolemia, atherosclerosis, hyperglycemia, diabetes type I, diabetes type II, insulin resistance, diabetic complications, sugar resistance dysfunction, X symptoms, heart failure, cardiovascular conditions, and for the modulation of appetite and food absorption of patients suffering from obesity, anorexia, bulimia and neurogenic anorexia.

The inventor has found that a compound having general formula (I) can be used to treat or prevent hPPARδ-mediated diseases, risk factors or conditions.

Therefore, an aspect of the present invention is to provide a compound of formula (I), or a pharmaceutically acceptable salt or solvate thereof:

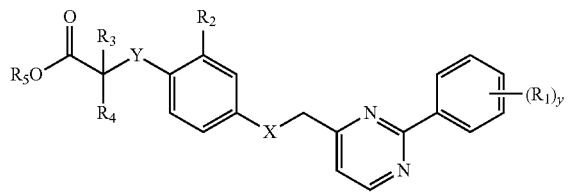

(I)

wherein:
$R_1$ each independently represents —$CF_3$ or halogen;
$R_2$ independently represents H, —$CH_3$, —$OCH_3$ or halogen;
$R_3$, $R_4$ independently represent H or —$CH_3$;
$R_5$ is selected from H, $C_1$-$C_6$ linear or branched alkyl or benzyl, the phenyl ring of the benzyl being optionally substituted by 1-5 substituents selected from the group consisting of halogen, nitro, hydroxyl, hydroxymethyl, trifluoromethyl, trifluoromethoxy, $C_1$-$C_6$ linear or branched alkyl, $C_2$-$C_6$ linear or branched alkenyl, $C_1$-$C_4$ alkoxy, $C_2$-$C_4$ alkenoxy, phenoxy, benzyloxy, nitrile group, carboxyl or amino;
y represents 0, 1, 2, 3, 4 or 5;
X represents O or S;
Y represents O or —$CH_2$—.

The compounds according to the present invention can activate hPPARδ.

A second aspect of the present invention is to provide a pharmaceutical composition comprising a compound of the present invention. The pharmaceutical composition of the present invention comprises at least one compound of formula (I), or pharmaceutically acceptable salt or solvate thereof, and at least one pharmaceutically acceptable carrier, diluent or excipient.

A third aspect of the present invention is to provide a method for preparing a compound of formula (I) or a pharmaceutically acceptable salt or solvate thereof.

A fourth aspect of the present invention is to provide the use of a compound of formula (I) or a pharmaceutically acceptable salt or solvate thereof for the preparation of a medicament for treating or preventing hPPARδ-mediated diseases, risk factors or conditions.

A fifth aspect of the present invention is to provide a method for treating or preventing hPPARδ-mediated diseases, risk factors or conditions, comprising administering subjects therapeutically or preventatively effective amount of a compound of the present invention.

hPPARδ-mediated diseases, risk factors or conditions include lipid abnormality, hyperlipidemia, hypercholesterolemia, atherosclerosis, hyperglycemia, diabetes type I, diabetes type II, insulin resistance, diabetic complications, sugar resistance dysfunction, X symptoms, heart failure, cardiovascular conditions, anorexia, bulimia and neurogenic anorexia.

Further, the present invention provides a compound of formula (I), or a pharmaceutically acceptable salt or solvate thereof:

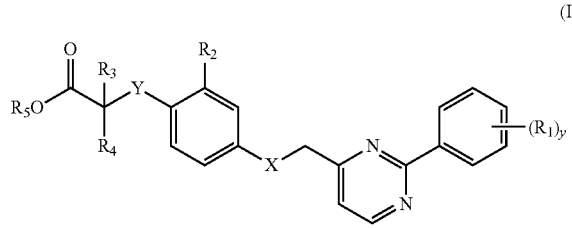

(I)

wherein:
$R_1$ each independently represents —$CF_3$ or halogen;
$R_2$ independently represents H, —$CH_3$, —$OCH_3$ or halogen;
$R_3$, $R_4$ independently represent H or —$CH_3$;
$R_5$ is selected from H, $C_1$-$C_6$ linear or branched alkyl or benzyl, the phenyl ring of the benzyl being optionally substituted by 1-5 substituents selected from the group consisting of halogen, nitro, hydroxyl, hydroxymethyl, trifluoromethyl, trifluoromethoxy, $C_1$-$C_6$ linear or branched alkyl, $C_2$-$C_6$ linear or branched alkenyl, $C_1$-$C_4$ alkoxy, $C_2$-$C_4$ alkenoxy, phenoxy, benzyloxy, nitrile group, carboxyl or amino;
y represents 0, 1, 2, 3, 4 or 5;
X represents O or S;
Y represents O or —$CH_2$—.

According to one preferred embodiment, the present invention relates to a compound of formula (II), or a pharmaceutically acceptable salt or solvate thereof:

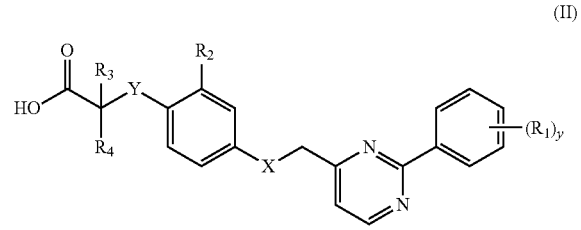

(II)

wherein:
$R_1$ each independently represents —$CF_3$ or halogen;
$R_2$ independently represents H, —$CH_3$, —$OCH_3$ or halogen;
$R_3$, $R_4$ independently represent H or —$CH_3$;
y represents 0, 1, 2, 3, 4 or 5;
X represents O or S;
Y represents O or —$CH_2$—.

According to one preferred embodiment of the present invention, in the compound of formula (I), Y represents O.

According to an other preferred embodiment of the present invention, in the compound of formula (I), X represents S.

According to another preferred embodiment of the present invention, in the compound of formula (I), $R_1$ represents —$CF_3$.

According to another preferred embodiment of the present invention, in the compound of formula (I), $R_2$ represents —$CH_3$.

According to another preferred embodiment of the present invention, in the compound of formula (I), $R_4$ represents H.

According to another preferred embodiment of the present invention, in the compound of formula (I), y represents 1.

According to another preferred embodiment of the present invention, in the compound of formula (I), the substituent $R_1$ is located at para position.

The preferred compounds of the present invention include:
{2-methyl-4-[2-(4-trifluoromethylphenyl)-pyrimidin-4-yl-methylthio]-phenoxy}-acetic acid;
{2-methyl-4-[2-(4-fluorophenyl)-pyrimidin-4-yl-methylthio]-phenoxy}-acetic acid;
{2-methyl-4-[2-(4-chlorophenyl)-pyrimidin-4-yl-methylthio]-phenoxy}-acetic acid;
{2-methyl-4-[2-(4-bromophenyl)-pyrimidin-4-yl-methylthio]-phenoxy}-acetic acid;
{2-methyl-4-[2-(2,4,6-trifluorophenyl)-pyrimidin-4-yl-methylthio]-phenoxy}-acetic acid;
{2-methyl-4-[2-(2,6-dichlorophenyl)-pyrimidin-4-yl-methylthio]-phenoxy}-acetic acid;
3-{4-[2-(4-trifluoromethylphenyl)-pyrimidin-4-yl-methoxy]-phenyl}-propionic acid;
3-{4-[2-(4-fluorophenyl)-pyrimidin-4-yl-methoxy]-phenyl}-propionic acid;
3-{4-[2-(4-chlorophenyl)-pyrimidin-4-yl-methoxy]-phenyl}-propionic acid;
3-{4-[2-(4-bromophenyl)-pyrimidin-4-yl-methoxy]-phenyl}-propionic acid;
3-{4-[2-(2,4,6-trifluorophenyl)-pyrimidin-4-yl-methoxy]-phenyl}-propionic acid;
3-{4-[2-(2,6-dichlorophenyl)-pyrimidin-4-yl-methoxy]-phenyl}-propionic acid;
2-methyl-2-{2-methyl-4-[2-(4-trifluoromethylphenyl)-pyrimidin-4-yl-methylthio]-phenoxy}-propionic acid;
2-methyl-2-{2-methyl-4-[2-(2,4,6-trifluorophenyl)-pyrimidin-4-yl-methylthio]-phenoxy}-propionic acid;
2-methyl-2-{2-methyl-4-[2-(4-fluorophenyl)-pyrimidin-4-yl-methylthio]-phenoxy}-propionic acid;
2-methyl-2-{2-methyl-4-[2-(4-chlorophenyl)-pyrimidin-4-yl-methylthio]-phenoxy}-propionic acid;
{4-[2-(4-trifluoromethylphenyl)-pyrimidin-4-yl-methoxy]-phenoxy}-acetic acid;
{4-[2-(4-fluorophenyl)-pyrimidin-4-yl-methoxy]-phenoxy}-acetic acid;
{4-[2-(4-chlorophenyl)-pyrimidin-4-yl-methoxy]-phenoxy}-acetic acid; and
{4-[2-(2,4,6-trifluorophenyl)-pyrimidin-4-yl-methoxy]-phenoxy}-acetic acid, or pharmaceutically acceptable salts or solvates thereof.

The compounds of the present invention can be prepared by following process, wherein the synthesis of A type intermediate and intermediates 9, 10 and 12 are illustrated in the examples.

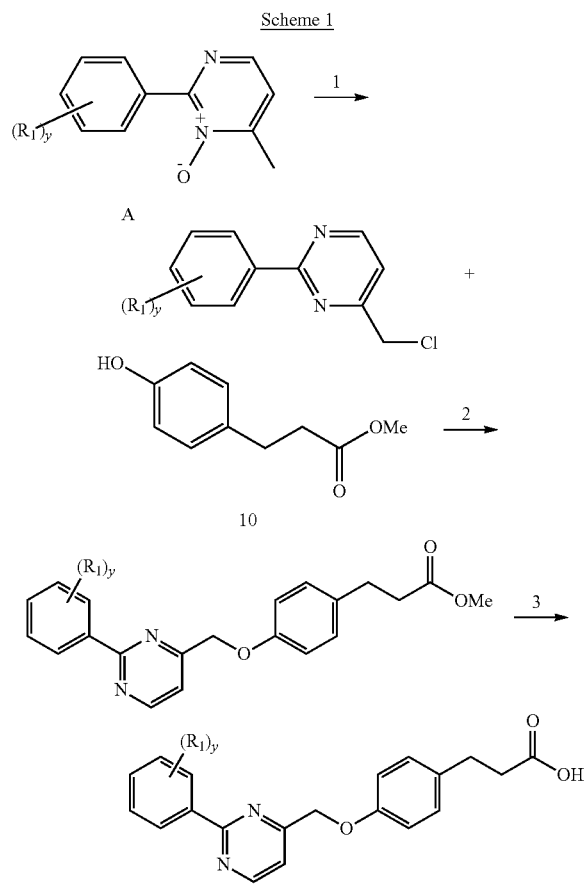

Scheme 1

Step 1: 4-chloromethyl-2-arylpyrimidine

To a 50 ml three-necked flask are added 4.85 mmol 2-aryl-4-methylpyrimidine 3-oxide, 10 ml dried dioxane, and then 14.55 mmol $POCl_3$. The mixture is refluxed at 100° C. for 1 hour. The solvent is removed by evaporation. To the residue is added water. The solution is extracted with ethyl acetate for three times, drying over anhydrous $MgSO_4$, filtration and evaporation, and is directly introduced into next step.

Step 2: Methyl 3-{4-[2-arylpyrimidin-4-yl-methoxy]-phenyl}-propionate

To a 50 ml three-necked flask are added 7.275 mmol NaH, 5 ml dried DMF. To the suspension of NaH is added dropwise 10 ml DMF containing 3.75 mmol intermediate 10. The suspension is stirred at room temperature for 30 minutes. To the stirred solution is added dropwise 5 ml DMF solution containing 4-chloromethyl-2-arylpyrimidine. The mixture is stirred at room temperature for 30 minutes. To the stirred solution is added water to produce precipitate. The product is collected by filtration and column chromatography (petroleum ether:ethyl acetate=5:1) to obtain methyl 3-{4-[2-arylpyrimidin-4-yl-methoxy]-phenyl}-propionate.

Step 3: 3-{4-[2-arylpyrimidin-4-yl-methoxy]-phenyl}-propionic acid 1 mmol methyl 3-{4-[2-arylpyrimidin-4-yl-methoxy]-phenyl}-propionate is dissolved in 5 ml THF. To the solution is added 2 ml 1 mol/L LiOH aqueous solution. The mixture is stirred at room temperature for 3 hours. Dilute HCl solution is added to adjust pH to weak acidity. The mixture is evaporated to remove tetrahydrofuran. The produced white solid is filtrated and recrystallized to obtain 3-{4-[2-arylpyrimidin-4-yl-methoxy]-phenyl}-propionic acid.

Scheme 2

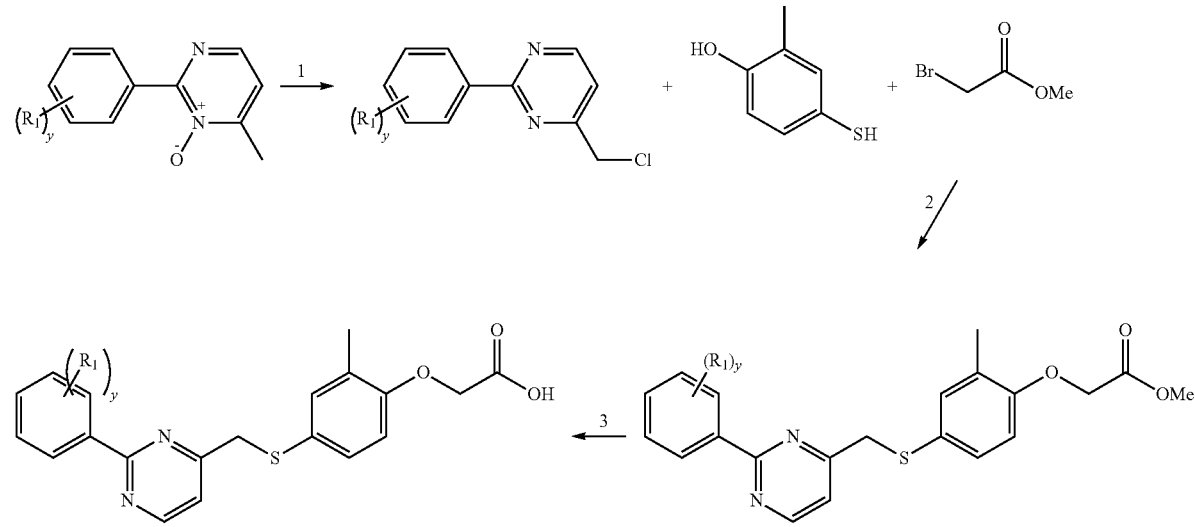

Step 1: Preparation of 4-chloromethyl-2-arylpyrimidine

To a 50 ml three-necked flask are added 7.274 mmol 2-aryl-4-methylpyrimidine 3-oxide, 10 ml dried dioxane and 21.82 mmol POCl$_3$. The mixture is refluxed at 100° C. for 1 hour. The solvent is removed by evaporation. To the residue is added water. The solution is extracted with ethyl acetate for three times. The extract is dried over anhydrous MgSO$_4$, filtrated and evaporated. The product is directly introduced into next step.

Step 2: Preparation of methyl {2-methyl-4-[2-arylpyrimidin-4-yl-methylthio]-phenoxy}-acetate 4.7 mmol 4-mercapto-2-methylphenol (12), 7.27 mmol Cs$_2$CO$_3$ and 10 ml acetonitrile are stirred at room temperature. To the stirred mixture is added 4-chloromethyl-2-arylpyrimidine (mixture). The mixture is stirred at room temperature for 5 hours. To the stirred mixture are added 7.05 mmol Cs$_2$CO$_3$ and 6.11 mmol methyl bromoacetate. The mixture is further stirred at room temperature for 5 hours. The mixture is filtered. The filtrate is evaporated. To the residue is added water. The solution is extracted with ethyl acetate for three times. The extract is dried over anhydrous MgSO$_4$, filtrated and purified by column chromatography to obtain methyl {2-methyl-4-[2-arylpyrimidin-4-yl-methylthio]-phenoxy}-acetate.

Step 3: Preparation of {2-methyl-4-[2-arylpyrimidin-4-yl-methylthio]-phenoxy}-acetic acid 1 mmol methyl {2-methyl-4-[2-arylpyrimidin-4-yl-methylthio]-phenoxy}-acetate is dissolved in 5 ml THF. To the solution is added 2 ml 1 mol/L LiOH aqueous solution. The mixture is stirred at room temperature for 3 hours. Dilute HCl solution is added to adjust pH to weak acidity. The mixture is evaporated to remove tetrahydrofuran. The produced white solid is filtrated and recrystallized to obtain {2-methyl-4-[2-arylpyrimidin-4-yl-methylthio]-phenoxy}-acetic acid.

Step 1: Preparation of 4-chloromethyl-2-arylpyrimidine

To a 50 ml three-necked flask is added 1.12 mmol 2-aryl-4-methylpyrimidine 3-oxide, 5 ml dried dioxane and 3.37 mmol POCl$_3$. The mixture is refluxed at 100° C. for 1 hour. The solvent is removed by evaporation. To the residue is added water. The solution is extracted with ethyl acetate for three times. The extract is dried over anhydrous MgSO$_4$, filtrated and evaporated. The solid is directly introduced into next step.

Step 2: Preparation of methyl {4-[2-arylpyrimidin-4-yl-methoxy]-phenoxy}-acetate To a 50 ml one-necked flask are added successively 0.784 mmol methyl (4-hydroxy-phenoxy)-acetate (9), 5 ml DMF, 2.4 mmol Cs$_2$CO$_3$ and 4-chloromethyl-2-arylpyrimidine (mixture). The mixture is heated to 80° C. and allowed to react for 2 hours. The reacted mixture is filtrated. To the filtrate is added water. The solution is extracted with ethyl acetate for three times. The extract is dried over anhydrous MgSO$_4$, filtrated, evaporated and recrystallized to obtain methyl {4-[2-arylpyrimidin-4-yl-methoxy]-phenoxy}-acetate.

Step 3: Preparation of {4-[2-arylpyrimidin-4-yl-methoxy]-phenoxy}-acetic acid 1 mmol methyl {4-[2-arylpyrimidin-4-yl-methoxy]-phenoxy}-acetate is dissolved in 5 ml THF. To the solution is added 2 ml 1 mol/L LiOH aqueous solution. The mixture is stirred at room temperature for 3 hours. Dilute HCl solution is added to adjust pH to weak acidity. The mixture is evaporated to remove tetrahydrofuran. The produced white solid is filtrated and recrystallized to obtain {4-[2-arylpyrimidin-4-yl-methoxy]-phenoxy}-acetic acid.

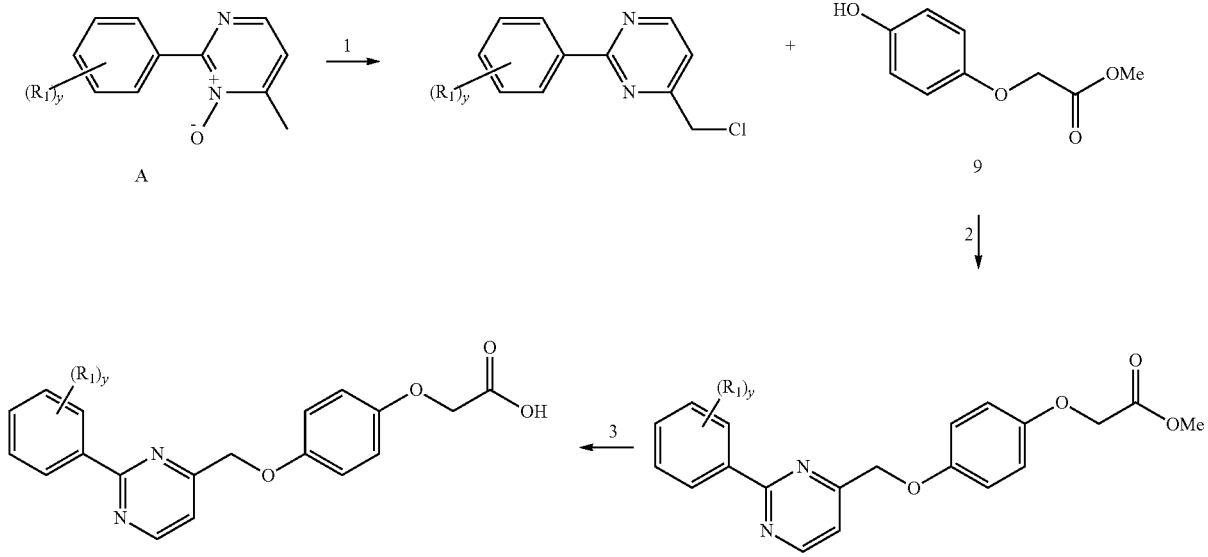

Scheme 3

Scheme 4

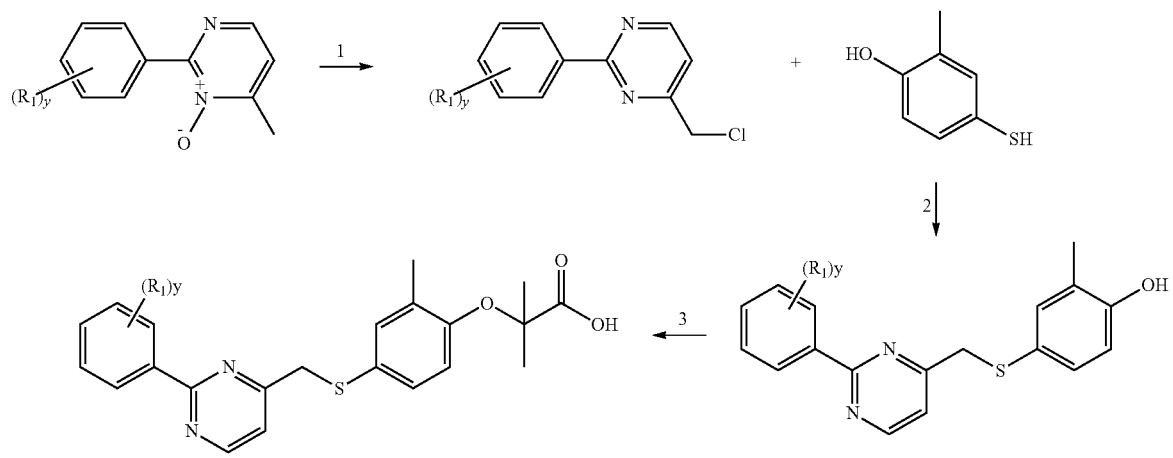

Step 1: Preparation of 4-chloromethyl-2-arylpyrimidine

To a 50 ml three-necked flask are added 0.83 mmol 2-aryl-4-methylpyrimidine 3-oxide, 5 ml dried dioxane, and then 2.49 mmol $POCl_3$. The mixture is refluxed at 100° C. for 1 hour. The solvent is removed by evaporation. To the residue is added water. The solution is extracted with ethyl acetate for three times. The extract is dried over anhydrous $MgSO_4$, filtrated and evaporated. The product is directly introduced into next step.

Step 2: preparation of 4-[2-arylpyrimidin-4-yl-methylthio]2-methylphenol

To a 50 ml three-necked flask are added 0.74 mmol 4-mercapto-2-methylphenol (12) dissolved in 5 ml dried dioxane, then 0.8 mmol $Cs_2CO_3$ is added. 4-Chloromethyl-2-arylpyrimidine is dissolved in 5 ml dried dioxane, and then added to the solution. The mixture is stirred at room temperature for 5 hours. The solvent is removed by evaporation. Dilute HCl solution is added to adjust pH to weak acidity. The solution is extracted with ethyl acetate for three times. The extract is dried over anhydrous $MgSO_4$, filtrated, evaporated and purified by column chromatograph to obtain 0.237 g 4-[2-arylpyrimidin-4-yl-methylthio]-2-methylphenol.

Step 3: Preparation of 2-methyl-2-{2-methyl-4-[2-arylpyrimidin-4-yl-methylthio]-phenoxy}-propionic acid To a 50 ml three-necked flask are added 2.2 mmol NaH and 2 ml dioxane. 0.54 mmol 4-[2-arylpyrimidin-4-yl-methylthio]-2-methylphenol is dissolved in 3 ml dried dioxane, and added slowly dropwise to the NaH suspension. The mixture is stirred at room temperature for 1 hour. To the mixture is added 0.54 mmol ethyl 2-bromo-2-methyl-propionate. The mixture is refluxed for 1 hour. The solvent is removed by evaporation. Dilute HCl solution is added to adjust pH to neutrality. The solution is extracted with ethyl acetate, drying over anhydrous $MgSO_4$, filtration, evaporation, column chromatograph to obtain 2-methyl-2-{2-methyl-4-[2-arylpyrimidin-4-yl-methylthio]-phenoxy}-propionic acid.

Those skilled in the art should be conscious of that the compounds of the present invention can be used in the form of pharmaceutically acceptable salts or solvates thereof. The pharmaceutically acceptable salts of the compounds of formula (I) or (II) include common salts formed with pharmaceutically acceptable inorganic acids or organic acids or inorganic bases or organic bases, and acid addition salts of quaternary ammonium. The examples of suitable salts formed with acids include the salts of hydrochloric acid, hydrobromic acid, sulfuric acid, phosphoric acid, nitric acid, perchloric acid, fumaric acid, acetic acid, propionic acid, succinic acid, glycolic acid, formic acid, lactic acid, maleic acid, tartaric acid, citric acid, embonic acid, malonic acid, hydroxymaleic acid, phenylacetic acid, glutamic acid, benzoic acid, salicylic acid, fumaric acid, tosylic acid, mesylic acid, naphthalene-2-sulfonic acid, benzenesulfonic acid, hydroxynaphthoic acid, hydroiodic acid, malic acid, tannic acid. Other acids, such as oxalic acid, although they are not pharmaceutically acceptable, they can be used for the preparation of salts as intermediates to obtain the compounds of the present invention and their pharmaceutically acceptable salts. The examples of suitable salts formed with bases include the salts of sodium, lithium, potassium, magnesium, aluminium, calcium, zinc, N,N'-dibenzylethylenediamine, procaine chloride, choline, diethanolamine, ethylenediamine, N-methylglucosamine and procaine. When the compounds of the present invention are mentioned hereinbelow, they include compounds of formula (I) or (II) and pharmaceutically acceptable salts or solvates thereof.

The present invention further includes the prodrugs of the compounds of the present invention. Once the prodrugs are administered, they are chemically transformed by metabolism and become drugs having activity. Generally, the prodrugs are functional derivatives of the compounds of the present invention, and they can be easily transformed in vivo into the desired compound of formula (I). For example, "Design of Prodrugs", edited H Bund Saard, Elsevier, 1985, described conventional processes to select and prepare suitable prodrugs derivatives.

The present invention also includes the active metabolites of the compounds of the present invention.

Another aspect of the present invention relates to a pharmaceutical composition comprising a compound of the present invention and at least one pharmaceutically acceptable carrier, diluent or excipient, which can be used in vivo treatment and has biocompatibility. Said pharmaceutical composition can be prepared into various forms in terms of different administration paths.

The pharmaceutical composition of the present invention includes effective dosage of the compound of formula (I) of the present invention or its pharmaceutically acceptable salts or solvates, such as hydrates, and one or more suitable pharmaceutically acceptable carriers, diluents or excipients. The pharmaceutically acceptable carriers, diluents or excipients include but are not limited to: ion exchangers, alumina, aluminium stearate, lecithin, serum protein, e.g. human serum albumin, buffers, e.g. phosphates, glycerin, sorbic acid, potassium sorbate, partial glycerin ester mixtures of saturated vegetable fatty acids, water, salts or electrolytes, e.g. protamine sulfate, disodium hydrogen phosphate, hydrogen potassium phosphate, sodium chloride, zinc salts, colloid silica, magnesium trisilicate, polyvinylpyrrolidone, cellulose materials, polyethylene alcohol, carboxylmethylcellulose sodium, polyacrylates, beeswax, lanolin.

The pharmaceutical composition of the present invention can be administered in any mode as described below: oral administration, spraying inhalation, rectal application, nasal application, buccal application, local application, non-intestinal application, such as subcutaneous, vein, muscle, intraperitoneal, intrathecal, intraventricular, intrasternal or intracal injection or importation, or by means of external reservoir, in which oral administration, intraperitoneal administration or intravenous injection administration are preferred.

When it is administered orally, the compound of the present invention can be prepared into any orally acceptable preparation form, including but being not limited to: tablets, capsules, aqueous solutions or aqueous suspensions. Wherein, the carries used in tablets generally include lactose and corn starch, besides, lubricants, e.g. magnesium stearate, can be added. The diluents used in capsules generally include lactose and dried corn starch. Aqueous suspensions generally refer to mixing active ingredients and suitable emulsifiers and suspending agents. If required, some sweeteners, flavors or colorants can be also added to the oral preparation form.

When topically applied, especially in the treatment of affected parts or organs where are easily reached by topically external application, such as, eyes, skin, the compounds of the present invention can be prepared into different topical application formulation forms in terms of different affected parts or organs, particularly described as follows:

When topically applied in eye part, the compounds of the present invention can be prepared into the formulation form of a micropowdered suspension or solution. The carrier used is isotonic sterile solution having certain pH with or without a preservative, such as benzyl alkylol chloride. For eye application, the compounds of the present invention can also be prepared into paste form, e.g. vaseline paste.

When topically applied in skin, the compounds of the present invention can be prepared into suitable ointment, lotion or cream form, wherein the active ingredient is suspended or dissolved in one or more carriers. The carriers which can be used in ointment formulation includes but is not limited to: mineral oil, liquid vaseline, albolene, propanediol, poly(ethylene oxide), poly(propylene oxide), emulsified wax and water; the carriers that can be used in lotion or cream include but are not limited to: mineral oil, sorbitan monostearic ester, Tween 60, cetane ester wax, hexadecene arylalcohol, 2-octyldodecanol, benzyl alcohol and water.

The compounds of the present invention can also be administered in sterile injection form, including sterile injection water or oil suspension or sterile injection solution, in which the carriers and solvents that can be used include water, Ringers solution and isotonic sodium chloride solution. Besides, sterile non-volatile oil can also be used as solvent or suspending medium, such as, monoglyceride or diglyceride.

Further, it should be pointed out that the application dosage and application method of the compounds of the present invention depend on various factors, including age, body weight, sex, natural health state and nutrition state of patients, the activity of the compounds applied, administration time, metabolism rate, order of severity of conditions and doctor's subjective judgment. The application dosage is preferably between 0.01 and 100 mg/kg body weight/day, most preferably between 5 and 10 mg/kg body weight/day.

EMBODIMENTS

Following intermediates and examples are used to further explain the present invention, however, the present invention is not limited by these intermediates and examples at any way.

The melting point of the compound is determined by means of YRT-3 melting instrument. The temperature is not revised. $^1$H-NMR spectrum is determined by means of Bruker ARX 400 nuclear magnetic resonance spectrometry. FAB, EI mass spectrum is determined by means of Micromass ZabSpec high resolution (1000) mass spectrometry.

Scheme A

General process for preparing of 2-aryl-4-methylpyrimidine 3-oxide from substituted arylbenzonitrile

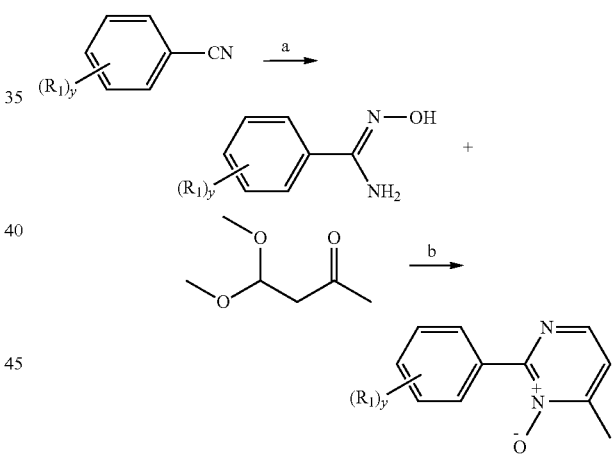

(a) To a 500 ml three-necked flask were added 0.1 mol arylbenzonitrile, 0.368 mol hydroxyamine hydrochloride, 0.19 mol Na$_2$CO$_3$, and a mixture of ethanol and water (35 ml ethanol, 300 ml water). The mixture was refluxed at 80° C. for 3 hours, cooled and stood to produce white crystal precipitate. The precipitate was dried to obtain aryl-N-hydroxylbenzamidine.

(b) 50.50 mmol Aryl-N-hydroxylbenzamidine, 55.55 mmol 4,4-dimethoxy-2-butanone, 5.25 ml TFA, 180 ml isopropanol were refluxed at 82° C. for 12 hours, cooled and evaporated to remove solvent. To the residue was added water. The solution was neutralized with saturated NaHCO$_3$ solution, extracted with ethyl acetate for three times. The extract was dried, filtrated, evaporated, and purified by column chromatograph (petroleum ether:ethyl acetate=4:1) to give 2-aryl-4-methylpyrimidine 3-oxide.

Intermediate 1: 2-(4-trifluoromethylphenyl)-4-methylpyrimidine 3-oxide

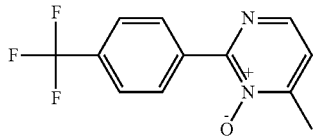

The title compound was prepared according to scheme A with 4-trifluoromethylbenzonitrile as starting material, and a white solid was obtained.

Intermediate 2: 2-(4-fluorophenyl)-4-methylpyrimidine 3-oxide

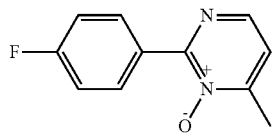

The title compound was prepared according to scheme A with p-fluorobenzonitrile as starting material, and a faint yellow solid was obtained.

Intermediate 3: 2-(4-chlorophenyl)-4-methylpyrimidine 3-oxide

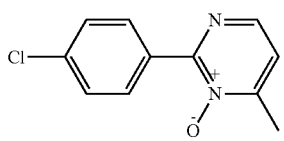

The title compound was prepared according to scheme A with 4-chlorobenzonitrile as starting material, and a white solid was obtained.

Intermediate 4: 2-(4-bromophenyl)-4-methylpyrimidine 3-oxide

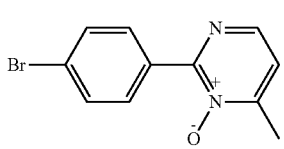

The title compound was prepared according to scheme A with 4-bromobenzonitrile as starting material, and a yellow solid was obtained.

Intermediate 5: 2-(2,4,6-trifluorophenyl)-4-methylpyrimidine 3-oxide

The title compound was prepared according to scheme A with 2,4,6-trifluorobenzonitrile as starting material, and a white solid was obtained.

Intermediate 6: 2-(2,6-dichlorophenyl)-4-methylpyrimidine 3-oxide

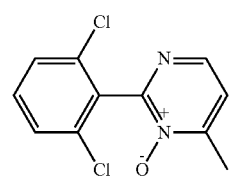

The title compound was prepared according to scheme A with 2,6-dichlorobenzonitrile as starting material, and a yellow solid was obtained.

Intermediate 7: Methyl (4-acetyl-phenoxy)-acetate

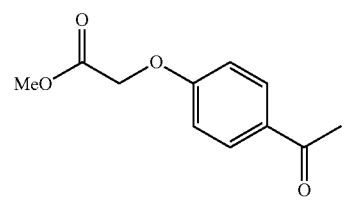

To a 100 ml two-necked flask were added 1.36 g p-hydroxyacetobenzene dissolved in 60 ml dried acetone, 12.43 g $K_2CO_3$, 0.14 g KI, and 4.0 ml methyl bromoacetate. The mixture was refluxed at 60° C. on oil bath for 3 hours, cooled, filtrated. The filtrate was stood over night to produce 1.756 g white acicular crystal, yield 84.42%. $^1$H-NMR (400 MHz, DMSO-$d_6$, δ ppm) δ 2.479 (3H, s), 3.663 (3H, s), 4.886 (2H, s), 7.005 (2H, d, J=8.8 Hz), 7.886 (2H, d, J=8.8 Hz).

Intermediate 8: Methyl (4-acetoxy-phenoxy)-acetate

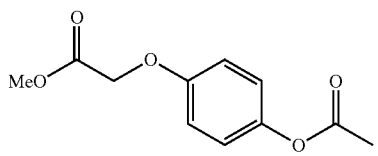 [SMILES: COC(=O)COc1ccc(OC(C)=O)cc1]

To a 100 ml three-necked flask were added 1.756 g methyl (4-acetoxy-phenoxy)-acetate, 20 ml CHCl$_3$ and 2.57 g m-chlorobenzoyl hydroperoxide. The mixture was refluxed at 60° C. for 18 hours, evaporated to remove solvent. To the residue was added ethyl acetate solvent. The solution is washed with KI, NaHSO$_3$ solution successively, dried, filtrated, and evaporated to obtain 1.512 g yellow solid, yield 80%.

Intermediate 9: Methyl (4-hydroxy-phenoxy)-acetate

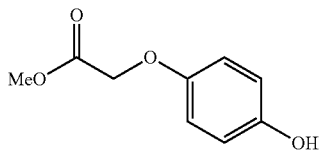 [SMILES: COC(=O)COc1ccc(O)cc1]

To a 100 ml round flask were added 1.512 g methyl (4-acetoxy-phenoxy)-acetate dissolved in 50 ml anhydrous methanol, 0.364 g sodium methoxide. The mixture was stirred at room temperature for 1 hour. To the stirred mixture was added dilute HCl to adjust pH to weak acidity. The solvent was removed by evaporation. To the residue was added water. The solution was extracted with ethyl acetate for three times. The extract was dried, filtrated and evaporated to obtain 1.004 g of a brown solid, yield 85%. $^1$H-NMR (400 MHz, DMSO-d$_6$, δ ppm) δ 3.679 (3H, s), 4.646 (2H, s), 6.672 (2H, d), 6.754 (2H, d), 9.0 (1H, s).

Intermediate 10: Methyl p-hydroxyphenpropionate

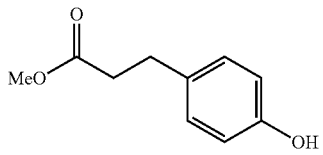 [SMILES: COC(=O)CCc1ccc(O)cc1]

4.61 g p-hydroxyphenpropionic acid, 50 ml methanol and 0.5 ml concentrated H$_2$SO$_4$ were refluxed at 70° C. for 3 hours and cooled. Excessive acid was neutralized with saturated NaHCO$_3$ solution. The neutralized solution was extracted with ethyl acetate for three times. The extract was dried, filtrated, evaporated and purified by column chromatograph (petroleum ether:ethyl acetate=2:1) to obtain 4.9 g white solid, yield 98%. $^1$H-NMR (400 MHz, DMSO-d$_6$, δ ppm) δ 2.5 (2H, m), 2.7 (2H, t), 3.567 (3H, s), 6.6 (2H, d, J=6.4 Hz), 7.0 (2H, d, J=8.4 Hz), 9.0 (1H, s).

Intermediate 11: 2-Methyl-4-thiocyano-phenol

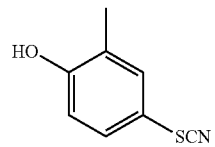

To a 250 ml flask were added 10.8 g o-methylphenol, 26.0 g sodium thiocyanate, 70 ml methanol, added dropwise 100 ml methanol solution containing 10.3 g NaBr, 5.3 ml liquid bromine at 0° C. under N$_2$ atmosphere. The mixture was stirred at room temperature for 3 hours. The mixture was neutralized with saturated NaHCO$_3$ solution, extracted with CH$_2$Cl$_2$ for four times. The extract was dried over anhydrous Na$_2$SO$_4$, filtrated, evaporated and purified by column chromatograph (petroleum ether:ethyl acetate=8:1) to obtain 11.1 g yellow solid, yield 67.27%. $^1$H-NMR (400 MHz, CDCl$_3$, δ ppm) δ 2.2558 (3H, s), 5.0 (1H, s), 6.8 (1H, d, J=8.4 Hz), 7.3605-7.2631 (1H, m), 7.3542 (1H, s).

Intermediate 12: 4-Mercapto-2-methylphenol

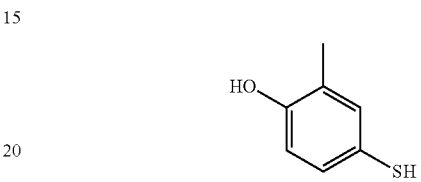

To a 100 ml round flask were added 0.3 g LiAlH$_4$ and 33 ml anhydrous tetrahydrofuran. To the LiAlH$_4$ suspension on ice bath was added dropwise 1.0 g 2-methyl-4-mercapto-phenol dissolved in tetrahydrofuran. Upon the completion of addition, the mixture was heated to room temperature and stirred for 3 hours. The reaction was stopped. To the mixture was added slowly water to destroy excessive LiAlH$_4$. The pH was adjusted to weak acidity. The solution was extracted with ethyl acetate for three times. The extract was dried over anhydrous Na$_2$SO$_4$, filtrated, evaporated and purified by column chromatograph (petroleum ether:ethyl acetate=4:1) to obtain 0.713 g white solid, yield 84%. $^1$H-NMR (400 MHz, DMSO-d$_6$, δ ppm) δ 2.0 (3H, s), 5.0 (1H, s), 6.6-6.7 (1H, d, J=8.4 Hz), 6.948-6.922 (1H, dd, J=2.4, 2.4 Hz), 7.015 (1H, s), 9.289 (1H, s).

EXAMPLES

Example 1

3-{4-[2-(4-fluorophenyl)-pyrimidin-4-yl-methoxy]-phenyl}-propionic acid

As described in scheme 1, the title compound as white solid was obtained with 2-(4-fluorophenyl)-4-methylpyrimidine 3-oxide as starting material, melting point: 167.2-168.0.

FAB-MS (m/z): 353.1 [M+H]$^+$; $^1$H-NMR (400 MHz, DMSO-d$_6$, δ ppm) δ 2.775-2.737 (2H, t), 5.268 (2H, s), 6.993-6.972 (2H, d, J=8.4 Hz), 7.183-7.162 (2H, d, J=8.4 Hz), 7.506-7.354 (3H, m), 8.470-8.433 (2H, m), 8.919-8.906 (1H, d, J=5.2 Hz), 12.128 (1H, s).

Example 2

3-{4-[2-(4-chlorophenyl)-pyrimidin-4-yl-methoxy]-phenyl}-propionic acid

As described in scheme 1, the title compound as white solid was obtained with 2-(4-chlorophenyl)-4-methylpyrimidine 3-oxide as starting material, melting point: 168.3-169.4.

FAB-MS (m/z): 369.1 [M]$^+$; $^1$H-NMR (400 MHz, DMSO-d$_6$, δ ppm) δ 2.7 (2H, t), 5.232 (2H, s), 6.953-6.932 (2H, d, J=8.4 Hz), 7.142-7.120 (2H, d, J=8.8 Hz), 7.588-7.477 (3H, m), 8.378-8.357 (2H, m), 8.894-8.881 (1H, d, J=5.2 Hz), 12.049 (1H, s).

Example 3

3-{4-[2-(4-bromophenyl)-pyrimidin-4-yl-methoxy]-phenyl}-propionic acid

As described in scheme 1, the title compound as white solid was obtained with 2-(4-bromophenyl)-4-methylpyrimidine 3-oxide as starting material, melting point: 168.0-168.8.

FAB-MS (m/z): 414.9 [M+H+1]$^+$; $^1$H-NMR (400 MHz, DMSO-d$_6$, δ ppm) δ 2.7 (2H, t), 5.272 (2H, s), 6.994-6.972 (2H, d, J=8.8 Hz), 7.183-7.162 (2H, d, J=8.4 Hz), 7.535-7.522 (1H, d, J=5.2 Hz), 7.768-7.746 (2H, m) 8.346-8.325 (2H, m), 8.932-8.919 (1H, d, J=5.2 Hz), 12.114 (1H, s).

Example 4

3-{4-[2-(4-trifluoromethylphenyl)-pyrimidin-4-yl-methoxy]-phenyl}-propionic acid As described in scheme 1, the title compound as white solid was obtained with 2-(4-trifluoromethylphenyl)-4-methylpyrimidine 3-oxide as starting material, melting point: 146.6-147.5.

FAB-MS (m/z): 403.2 [M+H]$^+$; $^1$H-NMR (400 MHz, DMSO-d$_6$, δ ppm) δ 2.7 (2H, t), 5.299 (2H, s), 7.004-6.982 (2H, d, J=8.8 Hz), 7.184-7.163 (2H, d, J=8.4 Hz), 7.595-7.582 (1H, d, J=5.2 Hz), 7.931-7.910 (2H, d, J=8.4 Hz) 8.606-8.586 (2H, d, J=8 Hz), 8.987-8.974 (1H, d, J=5.2 Hz), 12.072 (1H, s).

Example 5

3-{4-[2-(2,4,6-trifluorophenyl)-pyrimidin-4-yl-methoxy]-phenyl}-propionic acid As described in scheme 1, the title compound as white solid was obtained with 2-(2,4,6-trifluorophenyl)-4-methylpyrimidine 3-oxide as starting material, melting point: 143.8-144.1.

FAB-MS (m/z): 389.2 [M+H]$^+$; $^1$H-NMR (400 MHz, DMSO-d$_6$, δ ppm) δ 2.7 (2H, t), 5.249 (2H, s), 6.980-6.958 (2H, d, J=8.8 Hz), 7.178-7.157 (2H, d, J=8.4 Hz), 7.418-7.375 (2H, t), 7.671-7.658 (1H, d, J=5.2 Hz) 9.005-8.992 (1H, d, J=5.2 Hz), 12.095 (1H, s).

Example 6

3-{4-[2-(2,6-dichlorophenyl)-pyrimidin-4-yl-methoxy]-phenyl}-propionic acid

As described in scheme 1, the title compound as white solid was obtained with 2-(2,6-dichlorophenyl)-4-methylpyrimidine 3-oxide as starting material, melting point: 154.1-156.2.

EI-MS (m/z): 402.2 [M−H]$^+$; $^1$H-NMR (400 MHz, DMSO-d$_6$, δ ppm) δ 2.7 (2H, t), 5.252 (2H, s), 6.966-6.945 (2H, d, J=8.4 Hz), 7.170-7.149 (2H, d, J=8.4 Hz), 7.682-7.541 (4H, m), 9.041-9.001 (1H, d, J=16 Hz), 12.021 (1H, s).

Example 7

{2-methyl-4-[2-(4-trifluoromethylphenyl)-pyrimidin-4-yl-methylthio]phenoxy}-acetic acid As described in scheme 2, the title compound as white solid was obtained with 2-(4-trifluoromethylphenyl)-4-methylpyrimidine 3-oxide as starting material, melting point: 159.3-160.2.

FAB-MS (m/z): 435.1 [M+H]$^+$; $^1$H-NMR (400 MHz, DMSO-d$_6$, δ ppm) δ 2.100 (3H, s), 4.269 (2H, s), 4.660 (2H, s), 6.770-6.748 (1H, d, J=8.8 Hz), 7.217-7.168 (2H, m), 7.440-7.426 (1H, d, J=5.6 Hz), 7.891-7.870 (2H, d, J=8.4 Hz), 8.462-8.441 (2H, d, J=8.4 Hz), 8.859-8.846 (1H, d, J=5.2 Hz), 13.007 (1H, s).

Example 8

{2-methyl-4-[2-(4-fluorophenyl)-pyrimidin-4-yl-methylthio]-phenoxy}-acetic acid As described in scheme 2, the title compound as white solid was obtained with 2-(4-fluorophenyl)-4-methylpyrimidine 3-oxide as starting material, melting pointing: 160.9-162.4.

FAB-MS (m/z): 385.0 [M+H]$^+$; $^1$H-NMR (400 MHz, DMSO-d$_6$, δ ppm) δ 2.113 (3H, s), 4.243 (2H, s), 4.671 (2H, s), 6.771-6.750 (1H, d, J=8.4 Hz), 7.357-7.171 (5H, m), 8.335-8.300 (2H, m), 8.791-8.779 (1H, d, J=4.8 Hz), 13.050 (1H, s).

Example 9

{2-methyl-4-[2-(4-chlorophenyl)-pyrimidin-4-yl-methylthio]-phenoxy}-acetic acid As described in scheme 2, the title compound as white solid was obtained with 2-(4-chlorophenyl)-4-methylpyrimidine 3-oxide as starting material, melting pointing: 159.1-159.9.

FAB-MS (m/z): 401.1 [M]$^+$; $^1$H-NMR (400 MHz, DMSO-d$_6$, δ ppm) δ 2.110 (3H, s), 4.240 (2H, s), 4.660 (2H, s), 6.770-6.749 (1H, d, J=8.4 Hz), 7.225-7.162 (2H, m), 7.372-7.360 (1H, d, J=4.8 Hz), 7.581-7.559 (2H, m), 8.283-8.262 (2H, m), 8.801-8.788 (1H, d, J=5.2 Hz), 12.962 (1H, s).

Example 10

{2-methyl-4-[2-(4-bromophenyl)-pyrimidin-4-yl-methylthio]-phenoxy}-acetic acid As described in scheme 2, the title compound as white solid was obtained with 2-(4-bromophenyl)-4-methylpyrimidine 3-oxide as starting material, melting pointing: 159.3-160.2.

FAB-MS (m/z): 447.1 [M+H+1]$^+$; $^1$H-NMR (400 MHz, DMSO-d$_6$, δ ppm) δ 2.108 (3H, s), 4.244 (2H, s), 4.666 (2H, s), 6.768-6.747 (1H, d, J=8.4 Hz), 7.225-7.162 (2H, m), 7.382-7.369 (1H, d, J=5.2 Hz), 7.726-7.704 (2H, m), 8.211-8.189 (2H, m), 8.802-8.790 (1H, d, J=4.8 Hz), 12.935 (1H, s).

Example 11

{2-methyl-4-[2-(2,4,6-trifluorophenyl)-pyrimidin-4-yl-methylthio]-phenoxy}-acetic acid As described in scheme 2, the title compound as white solid was obtained with 2-(2,4,6-trifluorophenyl)-4-methylpyrimidine 3-oxide as starting material, melting pointing: 149.0-150.0.

FAB-MS (m/z): 421.1 [M+H]$^+$; $^1$H-NMR (400 MHz, DMSO-d$_6$, δ ppm) δ 2.100 (3H, s), 4.239 (2H, s), 4.663 (2H, s), 6.74-6.72 (1H, d, J=8.4 Hz), 7.3 (2H, m), 7.4 (3H, m), 8.85-8.82 (1H, d, J=12.4 Hz), 12.998 (1H, s).

Example 12

{2-methyl-4-[2-(2,6-difluorophenyl)-pyrimidin-4-yl-methylthio]-phenoxy}-acetic acid As described in scheme 2, the title compound as white solid was obtained with 2-(2,6-difluorophenyl)-4-methylpyrimidine 3-oxide as starting material, melting pointing: 138.1-139.3.

EI-MS (m/z): 434.1 [M−H]$^+$; $^1$H-NMR (400 MHz, DMSO-d$_6$, δ ppm) δ 2.093 (3H, s), 4.227 (2H, s), 4.656 (2H, s), 6.728-6.706 (1H, d, J=8.8 Hz), 7.15-7.07 (2H, m), 7.61-7.46 (4H, m), 8.851-8.838 (1H, d, J=5.2 Hz), 12.971 (1H, s).

Example 13

{4-[2-(4-trifluoromethylphenyl)-pyrimidin-4-yl-methoxy]-phenoxy}-acetic acid

As described in scheme 3, the title compound as white solid was obtained with 2-(4-trifluoromethylphenyl)-4-methylpyrimidine 3-oxide as starting material.

EI-MS (m/z): 404.1 [M]$^+$; $^1$H-NMR (400 MHz, DMSO-d$_6$, δ ppm) δ 4.604 (2H, s), 5.276 (2H, s), 6.899-6.867 (2H, m), 7.033-7.011 (2H, m), 7.607-7.594 (1H, d, J=5.2 Hz), 7.936-7.915 (2H, d, J=8.4 Hz), 8.609-8.588 (2H, d, J=8.4 Hz), 8.993-8.980 (1H, d, J=5.2 Hz), 12.925 (1H, s).

Example 14

{4-[2-(4-fluorophenyl)-pyrimidin-4-yl-methoxy]-phenoxy}-acetic acid

As described in scheme 3, the title compound as white solid was obtained with 2-(4-fluorophenyl)-4-methylpyrimidine 3-oxide as starting material, melting pointing: 180.0-181.1.

EI-MS (m/z): 354.0 [M−H−1]$^+$; $^1$H-NMR (400 MHz, DMSO-d$_6$, δ ppm) δ 4.528 (2H, s), 5.228 (2H, s), 6.866-6.842 (2H, d, J=9.6 Hz), 7.008-6.985 (2H, m, J=9.2 Hz), 7.507-7.341 (3H, m), 8.462-8.426 (2H, m), 8.910-8.897 (1H, d, J=5.2 Hz).

Example 15

{4-[2-(4-chlorophenyl)-pyrimidin-4-yl-methoxy]-phenoxy}-acetic acid

As described in scheme 3, the title compound as white solid was obtained with 2-(4-chlorophenyl)-4-methylpyrimidine 3-oxide as starting material, melting pointing: 180.1-182.3.

EI-MS (m/z): 370.0 [M−H]$^+$; $^1$H-NMR (400 MHz, DMSO-d$_6$, δ ppm) δ 4.512 (2H, s), 5.231 (2H, s), 6.864-6.841 (2H, m), 7.009-6.986 (2H, m), 7.531-7.518 (1H, d, J=5.2 Hz), 7.623-7.600 (2H, m), 8.413-8.391 (2H, m), 8.925-8.912 (1H, d, J=5.2 Hz).

Example 16

{4-[2-(2,4,6-trifluorophenyl)-pyrimidin-4-yl-methoxy]-phenoxy}-acetic acid

As described in scheme 3, the title compound as white solid was obtained with 2-(2,4,6-trifluorophenyl)-4-methylpyrimidine 3-oxide as starting material, melting pointing: 176.5-178.3.

EI-MS (m/z): 390.1 [M]$^+$; $^1$H-NMR (400 MHz, DMSO-d$_6$, δ ppm) δ 4.600 (2H, s), 5.221 (2H, s), 6.883-6.860 (2H, m), 7.011-6.979 (2H, m), 7.404-7.361 (2H, m), 7.678-7.666 (1H, d, J=4.8 Hz), 9.005-8.992 (1H, d, J=5.2 Hz), 12.938 (1H, s).

Example 17

2-methyl-2-{2-methyl-4-[2-(4-chlorophenyl)-pyrimidin-4-yl-methylthio]-phenoxy}-propionic acid As described in scheme 4, the title compound as white solid was obtained with 2-(4-chlorophenyl)-4-methylpyrimidine 3-oxide as starting material, melting pointing: 137.3-140.1.

EI-MS (m/z): 428.2 [M−H]$^+$; $^1$H-NMR (400 MHz, DMSO-d$_6$, δ ppm) δ 1.462 (6H, s), 2.079 (3H, s), 4.248 (2H, s), 6.620-6.599 (1H, d, J=8.4 Hz), 7.148-7.121 (1H, dd, J=2.4, 2.4 Hz), 7.232-7.227 (1H, d, J=2 Hz), 7.382-7.369 (1H, d, J=5.2 Hz), 7.578-7.556 (2H, m), 8.290-8.268 (2H, m), 8.803-8.790 (1H, d, J=5.2 Hz), 13.012 (1H, s).

Example 18

2-methyl-2-{2-methyl-4-[2-(4-fluorophenyl)-pyrimidin-4-yl-methylthio]-phenoxy}-propionic acid As described in scheme 4, the title compound as white solid was obtained with 2-(4-chlorophenyl)-4-methylpyrimidine 3-oxide as starting material, melting pointing: mp: 139.5-140.4.

EI-MS (m/z): 412.3 [M]$^+$; $^1$H-NMR (400 MHz, DMSO-d$_6$, δ ppm) δ 1.526 (6H, s), 2.143 (3H, s), 4.309 (2H, s), 6.676-6.655 (1H, d, J=8.4 Hz), 7.216-7.189 (1H, dd, J=2.4, 2 Hz), 7.304-7.299 (1H, d, J=2 Hz), 7.426-7.369 (3H, m), 8.402-8.364 (2H, m), 8.854-8.841 (1H, d, J=5.2 Hz), 13.012 (1H, s).

Example 19

2-methyl-2-{2-methyl-4-[2-(2,4,6-trifluorophenyl)-pyrimidin-4-yl-methylthio]-phenoxy}-propionic acid As described in scheme 4, the title compound as white solid was obtained with 2-(2,4,6-trifluorophenyl)-4-methylpyrimidine 3-oxide as starting material, melting pointing: 117.3-118.5.

FAB-MS (m/z): 449.0 [M+H]$^+$; $^1$H-NMR (400 MHz, DMSO-d$_6$, δ ppm) δ 1.471 (6H, s), 2.075 (3H, s), 4.241 (2H, s), 6.606-6.585 (1H, d, J=8.4 Hz), 7.094-7.068 (1H, dd, J=2, 2 Hz), 7.169-7.164 (1H, d, J=2 Hz), 7.491-7.477 (3H, m), 8.856-8.843 (1H, d, J=5.2 Hz), 13.006 (1H, s).

Example 20

2-methyl-2-{2-methyl-4-[2-(4-trichloromethylphenyl)-pyrimidin-4-yl-methylthio]-phenoxy}-propionic acid As described in scheme 4, the title compound as white solid was obtained with 2-(4-trifluoromethylphenyl)-4-methylpyrimidine 3-oxide as starting material, melting pointing: 143.4-144.9.

FAB-MS (m/z): 463.0 [M+H]$^+$; $^1$H-NMR (400 MHz, DMSO-d$_6$, δ ppm) δ 1.447 (6H, s), 2.062 (3H, s), 4.269 (2H, s), 6.614-6.593 (1H, d, J=8.4 Hz), 7.149-7.123 (1H, dd, J=2, 2 Hz), 7.220-7.215 (1H, d, J=2 Hz), 7.451-7.439 (1H, d, J=4.8 Hz), 7.887-7.865 (2H, d, J=8.8 Hz), 8.462-8.441 (2H, d, J=8.4 Hz), 8.862-8.848 (1H, d, J=5.6 Hz), 13.004 (1H, s).

Transfection Determination

The functional titration of the transient transfection of the compounds in HEK-293 cells was screened to determine their ability to activate PPAR subtype. Chimeric acceptor system was built in advance to compare relative transcription activity of acceptor subtype to same target gene and prevent the complexness of endogenous acceptor activation due to the explanation of results. Ligand binding domain of human PPARδ was fused to yeast transcription factor GAL4DNA binding domain, and then linked to expression carrier pM of mammal to build pM-hPPARδ/GAL4 plasmids. GAL4DNA binding region was connected to pB4-tk-luc to pB4-RES-tk-luc (a report gene of firefly luciferin enzyme containing 5 templates of GAL4DNA binding site). pRL-CMV-Rluc was used as internal standard to correct transfection efficiency and endogenous influence and reduce experimental error.

HEK-293 cells were grown in 48 wells plate, the density of cells was $2\text{-}4\times10^4$/well. The culture medium was 1640 of 10% defatted FCS free of phenol red and antibiotics. After 48 hours, the culture medium was changed as 1640 of 5% defatted FCS free of phenol red and antibiotics, and then pM-hPPARδ/GAL4, pB4-RES-tk-luc and pRL-CMV-Rluc plasmids were co-transfected in HEK-293 cells. The drug was administered after 24 hours, and the luminous intensity of luciferin enzyme was determined 24 hours after administration. The control was 0.2% DMSO. GW501516 was used as positive control drug. The results were shown in Table 1.

TABLE 1

Activation of part of compounds for PPARδ (1 μM)

| Compounds | GW501516 | example 7 | example 8 | example 9 | example 10 | example 17 | example 18 | example 20 |
|---|---|---|---|---|---|---|---|---|
| Activation ability % | 100 | 94.86 | 135.46 | 88.35 | 108.55 | 119.51 | 103.26 | 144.86 |

The invention claimed is:

1. A compound of formula (I):

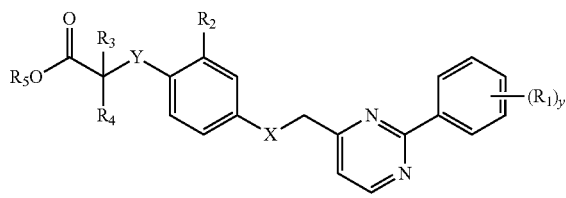

(I)

or a pharmaceutically acceptable salt or solvate thereof, wherein:
$R_1$ each independently represents —$CF_3$ or halogen;
$R_2$ independently represents H, —$CH_3$, —$OCH_3$ or halogen;
$R_3$, $R_4$ independently represent H or —$CH_3$;
$R_5$ is selected from H, $C_1$-$C_6$ linear or branched alkyl or benzyl, the phenyl ring of the benzyl being optionally substituted by 1-5 substituents selected from the group consisting of halogen, nitro, hydroxyl, hydroxymethyl, trifluoromethyl, trifluoromethoxy, $C_1$-$C_6$ linear or branched alkyl, $C_2$-$C_6$ linear or branched alkenyl, $C_1$-$C_4$ alkoxy, $C_2$-$C_4$ alkenoxy, phenoxy, benzyloxy, nitrile group, carboxyl or amino;
y represents 0, 1, 2, 3, 4 or 5;
X represents O or S; and
Y represents O.

2. The compound according to claim 1, or a pharmaceutically acceptable salt or solvate thereof, wherein $R_5$ is H.

3. The compound according to claim 1 or 2, or a pharmaceutically acceptable salt or solvate thereof, wherein y is 1.

4. The compound according to claim 1 or 2, or a pharmaceutically acceptable salt or solvate thereof, wherein $R_1$ is located at para position.

5. The compound of claim 1, wherein the compound is selected from a group consisting of:
{2-methyl-4-[2-(4-trifluoromethylphenyl)-pyrimidin-4-yl-methylthio]-phenoxy}-acetic acid;
{2-methyl-4-[2-(4-fluorophenyl)-pyrimidin-4-yl-methylthio]-phenoxy}-acetic acid;
{2-methyl-4-[2-(4-chlorophenyl)-pyrimidin-4-yl-methylthio]-phenoxy}-acetic acid;
{2-methyl-4-[2-(4-bromophenyl)-pyrimidin-4-yl-methylthio]-phenoxy}-acetic acid;
{2-methyl-4-[2-(2,4,6-trifluorophenyl)-pyrimidin-4-yl-methylthio]-phenoxy}-acetic acid;
{2-methyl-4-[2-(2,6-dichlorophenyl)-pyrimidin-4-yl-methylthio]-phenoxy}-acetic acid;
2-methyl-2-{2-methyl-4-[2-(4-trifluoromethylphenyl)-pyrimidin-4-yl-methylthio]-phenoxy}-propionic acid;
2-methyl-2-{2-methyl-4-[2-(2,4,6-trifluorophenyl)-pyrimidin-4-yl-methylthio]-phenoxy}-propionic acid;
2-methyl-2-{2-methyl-4-[2-(4-fluorophenyl)-pyrimidin-4-yl-methylthio]-phenoxy}-propionic acid;
2-methyl-2-{2-methyl-4-[2-(4-chlorophenyl)-pyrimidin-4-yl-methylthio]-phenoxy}-propionic acid;
{4-[2-(4-trifluoromethylphenyl)-pyrimidin-4-yl-methoxy]-phenoxy}-acetic acid;
{4-[2-(4-fluorophenyl)-pyrimidin-4-yl-methoxy]-phenoxy}-acetic acid;
{4-[2-(4-chlorophenyl)-pyrimidin-4-yl-methoxy]-phenoxy}-acetic acid; and
{4-[2-(2,4,6-trifluorophenyl)-pyrimidin-4-yl-methoxy]-phenoxy}-acetic acid; or a pharmaceutically acceptable salt or solvate thereof.

6. A pharmaceutical composition comprising the compound according to claim 1 or a pharmaceutically acceptable salt or solvate thereof, and at least one pharmaceutically acceptable carrier, diluent or excipient.

7. A compound of formula (I):

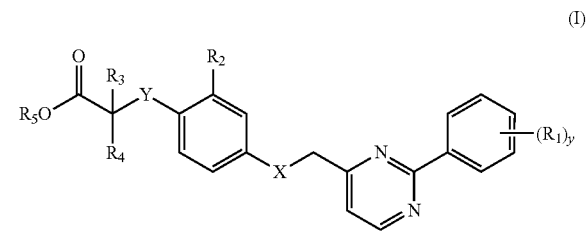

(I)

or a pharmaceutically acceptable salt or solvate thereof, wherein:
$R_1$ each independently represents —$CF_3$ or halogen;
$R_2$ independently represents H, —$CH_3$, —$OCH_3$ or halogen;
$R_3$, $R_4$ independently represent H or —$CH_3$;

$R_5$ is selected from H, $C_1$-$C_6$ linear or branched alkyl or benzyl, the phenyl ring of the benzyl being optionally substituted by 1-5 substituents selected from the group consisting of halogen, nitro, hydroxyl, hydroxymethyl, trifluoromethyl, trifluoromethoxy, $C_1$-$C_6$ linear or branched alkyl, $C_2$-$C_6$ linear or branched alkenyl, $C_1$-$C_4$ alkoxy, $C_2$-$C_4$ alkenoxy, phenoxy, benzyloxy, nitrile group, carboxyl or amino;

y represents 0, 1, 2, 3, 4 or 5;

X represents S; and

Y represents O or —$CH_2$—.

8. The compound according to claim 7, or a pharmaceutically acceptable salt or solvate thereof, wherein $R_5$ is H.

9. The compound according to claim 7, or a pharmaceutically acceptable salt or solvate thereof, wherein y is 1.

10. The compound according to claim 7, or a pharmaceutically acceptable salt or solvate thereof, wherein $R_1$ is located at para position.

11. The compound of claim 7, wherein the compound is selected from a group consisting of:

{2-methyl-4-[2-(4-trifluoromethylphenyl)-pyrimidin-4-yl-methylthio]-phenoxy}-acetic acid;

{2-methyl-4-[2-(4-fluorophenyl)-pyrimidin-4-yl-methylthio]-phenoxy}-acetic acid;

{2-methyl-4-[2-(4-chlorophenyl)-pyrimidin-4-yl-methylthio]-phenoxy}-acetic acid;

{2-methyl-4-[2-(4-bromophenyl)-pyrimidin-4-yl-methylthio]-phenoxy}-acetic acid;

{2-methyl-4-[2-(2,4,6-trifluorophenyl)-pyrimidin-4-yl-methylthio]-phenoxy}-acetic acid;

{2-methyl-4-[2-(2,6-dichlorophenyl)-pyrimidin-4-yl-methylthio]-phenoxy}-acetic acid;

2-methyl-2-{2-methyl-4-[2-(4-trifluoromethylphenyl)-pyrimidin-4-yl-methylthio]-phenoxy}-propionic acid;

2-methyl-2-{2-methyl-4-[2-(2,4,6-trifluorophenyl)-pyrimidin-4-yl-methylthio]-phenoxy}-propionic acid;

2-methyl-2-{2-methyl-4-[2-(4-fluorophenyl)-pyrimidin-4-yl-methylthio]-phenoxy}-propionic acid; and 2-methyl-2-{2-methyl-4-[2-(4-chlorophenyl)-pyrimidin-4-yl-methylthio]-phenoxy}-propionic acid;

or a pharmaceutically acceptable salt or solvate thereof.

12. A pharmaceutical composition comprising the compound according to claim 7 or a pharmaceutically acceptable salt or solvate thereof, and at least one pharmaceutically acceptable carrier, diluent or excipient.

13. A method for treating an hPPARδ-mediated disease or condition in an individual, the method comprising the step of administering to the individual the compound of claim 1 or a pharmaceutically acceptable salt or solvate thereof, wherein the hPPARδ-mediated disease or condition is selected from a group consisting of lipid abnormality, hyperlipidemia, hypercholesterolemia, atherosclerosis, hyperglycemia, diabetes type I, diabetes type II, insulin resistance, diabetic complications, sugar resistance dysfunction, and obesity.

14. A method for treating an hPPARδ-mediated disease or condition in an individual, the method comprising the step of administering to the individual the compound of claim 7 or a pharmaceutically acceptable salt or solvate thereof, wherein the hPPARδ-mediated disease or condition is selected from a group consisting of lipid abnormality, hyperlipidemia, hypercholesterolemia, atherosclerosis, hyperglycemia, diabetes type I, diabetes type II, insulin resistance, diabetic complications, sugar resistance dysfunction, and obesity.

* * * * *

UNITED STATES PATENT AND TRADEMARK OFFICE
CERTIFICATE OF CORRECTION

PATENT NO. : 8,759,355 B2  
APPLICATION NO. : 12/670464  
DATED : June 24, 2014  
INVENTOR(S) : Song Li et al.

Page 1 of 1

It is certified that error appears in the above-identified patent and that said Letters Patent is hereby corrected as shown below:

On the Title Page

Left column, before item (51), insert a new item as follows:

item --(30) Foreign Application Priority Data
  July 25, 2007 (CN)  2007 10129735.4--.

Signed and Sealed this

Thirty-first Day of March, 2015

Michelle K. Lee
*Director of the United States Patent and Trademark Office*